United States Patent
Lashinski et al.

(10) Patent No.: US 6,309,411 B1
(45) Date of Patent: Oct. 30, 2001

(54) METHOD AND APPARATUS TO PREVENT STENT MIGRATION

(75) Inventors: Robert Lashinski, Windsor; Bradley Jendersee, Petaluma; Michael D. Boneau, Sunnyvale, all of CA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 0 days.

(21) Appl. No.: 09/092,623

(22) Filed: Jun. 5, 1998

Related U.S. Application Data

(63) Continuation of application No. 08/562,138, filed on Nov. 22, 1995, now abandoned, which is a continuation-in-part of application No. 08/326,031, filed on Oct. 19, 1994, now abandoned.

(51) Int. Cl.$^7$ .......................................... A61F 2/00
(52) U.S. Cl. ..................... 623/1.1; 623/1.36; 623/1.39
(58) Field of Search ................... 623/1, 11, 12; 606/191–200, 1.1, 1.36, 1.39

(56) References Cited

U.S. PATENT DOCUMENTS

| | | | |
|---|---|---|---|
| 4,577,631 | * | 3/1986 | Kreamer ................................ 623/1 |
| 4,655,771 | | 4/1987 | Wallsten . |
| 4,733,665 | | 3/1988 | Palmaz . |
| 4,776,337 | | 10/1988 | Palmaz . |
| 4,938,740 | | 7/1990 | Melbin . |
| 4,955,859 | * | 9/1990 | Zilber ..................................... 604/8 |
| 5,015,253 | | 5/1991 | MacGregor . |
| 5,019,090 | | 5/1991 | Pinchuk . |
| 5,052,998 | | 10/1991 | Zimmon . |
| 5,100,429 | * | 3/1992 | Sinofsky et al. ..................... 623/1 |
| 5,167,614 | | 12/1992 | Tessmann et al. .................... 604/8 |
| 5,167,714 | * | 12/1992 | Tessmann et al. .................... 623/1 |
| 5,236,446 | * | 8/1993 | Dumon ................................... 623/1 |
| 5,292,331 | * | 3/1994 | Boneau ................................... 623/1 |
| 5,423,885 | | 6/1995 | Williams ............................... 623/1 |
| 5,549,635 | | 8/1996 | Solar . |
| 5,628,788 | | 5/1997 | Pinchuk . |
| 5,653,747 | | 8/1997 | Dereume . |
| 5,718,713 | | 2/1998 | Frantzen .............................. 606/198 |

FOREIGN PATENT DOCUMENTS

| | | |
|---|---|---|
| A 61333/90 | 2/1991 | (AU) . |
| 0 497 620 A2 | 8/1992 | (EP) . |
| 0 539 237 A1 | 4/1993 | (EP) . |
| 0 797 963 A2 | 10/1997 | (EP) . |
| 0 850 604 A2 | 7/1998 | (EP) ...................................... 623/1 |
| WO 89/07916 | 9/1989 | (WO) . |
| WO 92/06734 | 4/1992 | (WO) . |
| WO 95/13033 | 5/1995 | (WO) . |

OTHER PUBLICATIONS

Papanicolaou, et al., "Insertion of a Biliary Endoprosthesis Using a Balloon Dilatation Catheter," *Gastrointestinal Radiology*, 1985; 10:394–396.

Rosch, et al., "Modified Gianturco Expandable Wire Stents in Experimental and Clinical Use," *Annales De Radiologie*, 1988; 31:2:100–103.

* cited by examiner

*Primary Examiner*—Michael J. Milano

(57) ABSTRACT

An endoprosthesis is provided having an expandable, generally cylindrical body portion defining an inside surface and an outside surface. The inside surface is preferably regular and smooth to yield a low coefficient of friction, while the outside surface is modified to yield a relatively high coefficient of friction with a vessel surface, includes a macroscopic surface modification to engage the vessel surface, or includes an adhesive coating that bonds the stent to the vessel surface.

7 Claims, 2 Drawing Sheets

METHOD AND APPARATUS TO PREVENT STENT MIGRATION

This application is a continuation of U.S. patent application Ser. No. 08/562,138, filed on Nov. 22, 1995, now abandoned which is a continuation-in-part of U.S. patent application Ser. No. 08/326,031, filed on Oct. 19, 1994, now abandoned.

FIELD OF THE INVENTION

This invention relates generally to medical devices, and more specifically to an improved implantable stent apparatus for the treatment of stenoses in coronary or peripheral vessels in humans.

BACKGROUND OF THE INVENTION

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

An important development for treating atherosclerosis and other forms of coronary narrowing is percutaneous transluminal coronary angioplasty, hereinafter referred to as "angioplasty" or "PTCA". The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

Unfortunately, while the affected artery can be enlarged, in some instances the vessel restenoses chronically, or closes down acutely, negating the positive effect of the angioplasty procedure. In the past, such restenosis has frequently necessitated repeat PTCA or open heart surgery. While such restenosis does not occur in the majority of cases, it occurs frequently enough that such complications comprise a significant percentage of the overall failures of the PTCA procedure, for example, twenty-five to thirty-five percent of such failures.

To lessen the risk of restenosis, various devices have been proposed for mechanically keeping the affected vessel open after completion of the angioplasty procedure. Such endoprostheses (generally referred to as "stents"), are typically inserted into the vessel, positioned across the lesion or stenosis, and then expanded to keep the passageway clear. The stent overcomes the natural tendency of the vessel walls of some patients to restenose, thus maintaining the patency of the vessel.

Various types of stents are currently under development, although to date none has proven completely satisfactory during testing. U.S. Pat. No. 4,655,771 to Wallsten describes a stent comprising a tube of stainless wire braid. During insertion, the tube is positioned along a delivery device, such as a catheter, in extended form, making the tube diameter as small as possible. When the stent is positioned across the lesion, it is expanded, causing the length of the tube to contract and the diameter to expand. Depending on the materials used in construction of the stent, the tube maintains the new shape either through mechanical force or otherwise.

U.S. Pat. No. 4,733,665 to Palmaz describes a stent comprising a slotted stainless steel cylinder that forms a mesh when expanded. The stent is delivered to an affected area by a balloon catheter, and is then expanded to the proper size by inflating the balloon.

A drawback of such previously known stents, however, is the tendency of such stents to migrate downstream from the initial placement area. For example, due to irregularity in the vessel diameter or underexpansion of the stent, such stents have been observed to migrate downstream from the initial placement area. Thus, not only is the objective of the stent implantation not achieved, but the migrating stent may cause injury elsewhere in the vascular system.

These and other complications have resulted in a low level of acceptance for such stents within the medical community for certain procedures, and to date stents have not been accepted as a practical method for treating many chronic restenosis conditions.

It would therefore be desirable to provide methods and apparatus, useful for treating chronic restenosis conditions, that retain an endoprosthesis in its area of initial placement, and which reduce the risk of migration of the endoprosthesis.

SUMMARY OF THE INVENTION

In view of the foregoing, it is an object of the present invention to provide methods and apparatus for treating chronic restenosis conditions that retain an endoprosthesis in its area of initial placement, and which reduce the risk of migration of the endoprosthesis.

The stent surface anchor constructed in accordance with this invention provides an improved endoprosthesis or stent having an expandable, generally cylindrical body portion defining an inside surface and an outside surface. In accordance with the present invention, the inside surface is preferably regular and smooth to yield a low coefficient of friction, while the outside surface is modified to yield a relatively high coefficient of friction with the vessel surface, includes a macroscopic surface modification to engage the vessel surface, or includes an adhesive coating that bonds with the vessel surface.

The deployment methods for implanting a stent constructed in accordance with the present invention include balloon expansion, self-expansion, self-retraction and mechanical expansion. Some of the intended uses include PTCA type stenting, PTA type stenting, graft support, graft delivery, INR use, GI tract use, drug delivery, and biliary stenting.

BRIEF DESCRIPTION OF THE INVENTION

Figure 1:
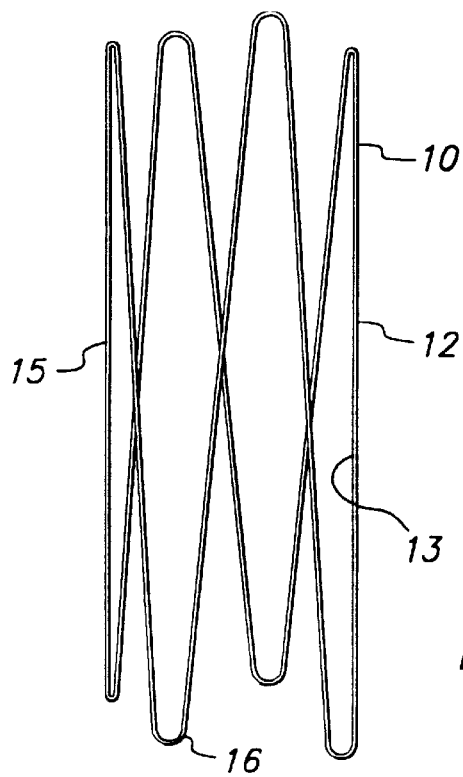
FIG. 1 is an elevational view of an illustrative stent constructed in accordance with the present invention.

In overview, an endoprothesis constructed in accordance with the present invention comprises a generally cylindrical body having a smooth inner surface and an outer surface capable of engaging the intima of a vessel. The methods and apparatus of the present invention are illustratively described with respect to the low-mass, unitary wire-like stent structure described in U.S. Pat. No. 5,292,331. It will of course be understood that the present invention is not limited to that stent structure, but is generally applicable to previously known stents to reduce the potential for migration of such stents.

As is generally known, intravascular (and other) stents are best utilized when the placement position is maintained beyond a point of endothelialization or fibrous encapsulation. Accordingly, vascular stents constructed in accordance with the present invention provide a smooth surface on the inside of the stent for unobstructed blood flow. Moreover, the use of a smooth inner surface for the stent reduces thrombogenicity.

Further in accordance with the present invention, the stent includes an irregular or modified outside surface for position maintenance. A number of methods may be used to improve the positional stability of a stent, including introducing a frictional force between the stent and the vessel wall, or alternatively, bonding the stent to the vessel wall.

In particular, a first method involves generating a frictional force $F_f$ between the outside surface of the stent and the inner surface of the vessel. The frictional force $F_f$ is a function of the frictional coefficient C between the two surfaces and the force pushing the two surfaces together $F_n$. Assuming that the normal force $F_n$ is unique and limited for most stents, the frictional coefficient is a property that may be varied to change the frictional force ($F_f=CF_n$). To increase the frictional coefficient, a somewhat microscopic, potentially irregular, non-smooth or changed outside surface is produced on the stent to modify the frictional coefficient. Frictional coefficient changes may be made by changing materials, or stent processing parameters such as electropolishing, machining, tumbling, sand blasting, sanding, etching and the like.

A second method of increasing the positional stability of an intravascular stent involves utilizing stent surface profiles that physically interleave with the intima of the vessel to mechanically prohibit stent migration. Macroscopic surface modifications may include, for example, grooves that increase the surface area in contact with the vessel, cross axial grooves, axial and cross-axial protrusions, crisscross protrusions and grooves, barbs, or even more pronounced versions of the features described in the preceding paragraph. These modifications may be employed over all or only a portion of the stent outer surface, thus yielding a type of peak/valley structural interaction that reduces the risk of stent movement.

Yet another method involves employing an adhesive-type coating that accomplishes any or all of the following: an increase in the coefficient of friction, a physical interleaving with the topography of the vessel, and/or the formation of an adhesive joint between the vessel and the stent. The coatings could be precured or uncured, and uncured coatings could be cured by a heat, time, UV light, visible light, and so forth.

Referring now to FIG. 1, a first illustrative embodiment of a low-mass, unitary wire-like stent 10, such as described in U.S. Pat. No. 5,292,331, and suitable for use in accordance with the present invention, is described. Stent 10 may be formed from a single piece of wire-like material that defines an expandable stent having an outside surface that is mechanically abraded or otherwise affected to create surface modifications yielding a series of peaks and valleys for mechanical interaction with the vessel wall, as described in detail hereinbelow.

Stent 10 preferably comprising an implantable quality high grade stainless steel, machined specially for intravascular applications, and may have its outside surface selectively plated with platinum to provide improved visibility during fluoroscopy. The cross-sectional shape of stent 10 may be circular, ellipsoidal, rectangular, hexagonal, square, or other polygon, and includes a plurality of axial bends that permit compression of the stent onto a delivery catheter, and subsequent expansion once in place at affected area.

Stent 10 may have a relatively crown-like shape, including a generally cylindrical body portion 15 defining inside surface 12 and outside surface 13. Cylindrical body portion 15 is formed with a plurality of generally straight wire-like sections that are joined one to another at a plurality of rounded apices 16. Inside surface 12 is preferably smooth and yields a low coefficient of friction, while outside surface 13 is preferably treated to provide a high coefficient of friction, as described hereinbelow.

In a preferred illustrative embodiment, stent 10 comprises a single piece of material, bent to form a plurality of upper axial turns and lower axial turns. The axial turns permit the stent to be compressed or expanded over a wide range while still retaining the capability to exert significant mechanical force as required to prevent a vessel from restenosing. Stent sizes for cardiovascular applications may range from one millimeter to two centimeters in length, and typically have a length in a range between 3.5 millimeters to 6 millimeters.

Figure 2A:
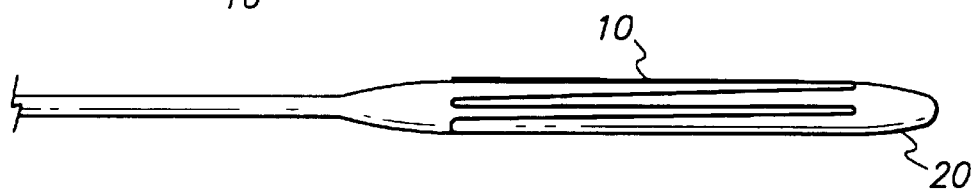
FIGS. 2A–2C show, respectively, the stent of FIG. 1 compressed onto the balloon catheter of a delivery system; the stent and balloon catheter positioned within a portion of a vessel; and the stent in its expanded form, positioned within the vessel.
Figure 2B:
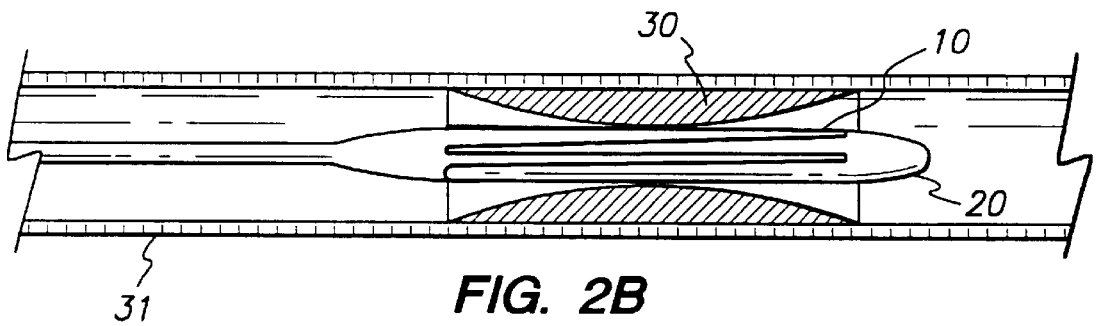
Figure 2C:
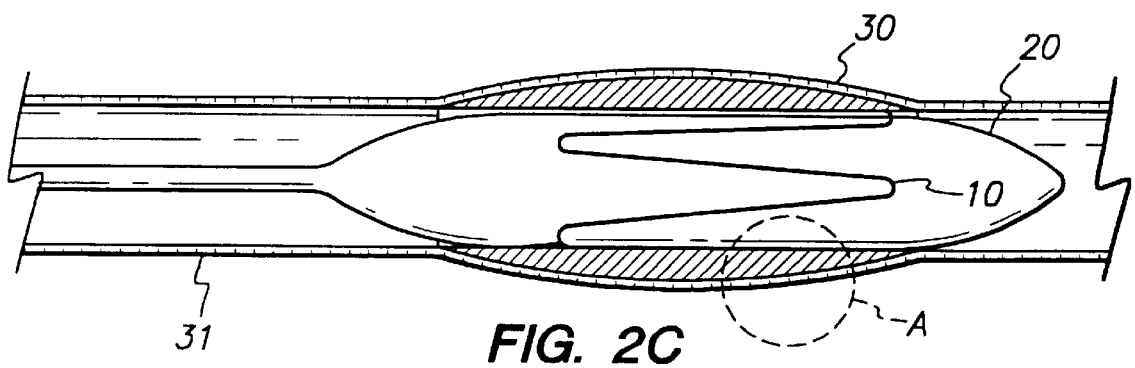

Referring now to FIGS. 2A–2C, stent 10 may be crimped onto the balloon of a balloon catheter for delivery to an affected region of a vessel. Alternatively, a sheath may be provided to cover and protect the balloon and stent during delivery into a vessel. This sheath is then removed prior to inflation of the balloon and expansion of the stent.

Using conventional stent position monitoring techniques, the delivery system is maneuvered to position the stent across stenosis 30 (see FIG. 2B). The balloon is then inflated to expand stent 10 into contact with the vessel wall, as shown in FIG. 2C. As stent 10 expands, it also causes stenosis 30 to expand, so that plaque deposited within the intima of the vessel is displaced and thinned. The stent thus becomes embedded in the plaque or other fibrotic material adhering to the intima of the vessel.

Figure 3A:
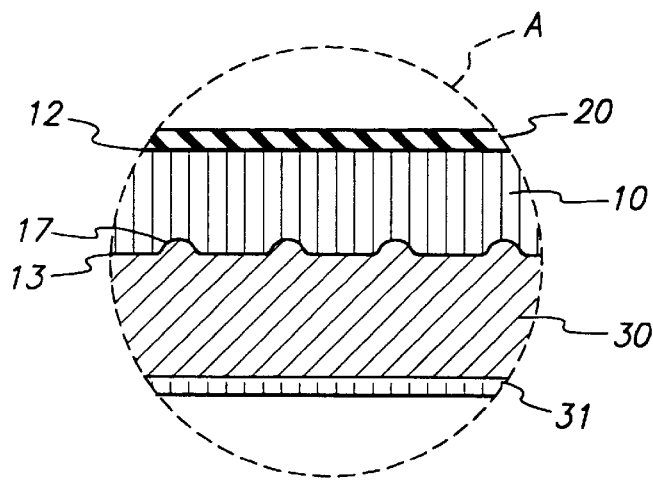
FIGS. 3A–3C are magnified cross-sectional views of area A of FIG. 2C, showing the interaction between the outside surface of the stent and interior surface of the vessel for three illustrative embodiments of the present invention.
Figure 3B:
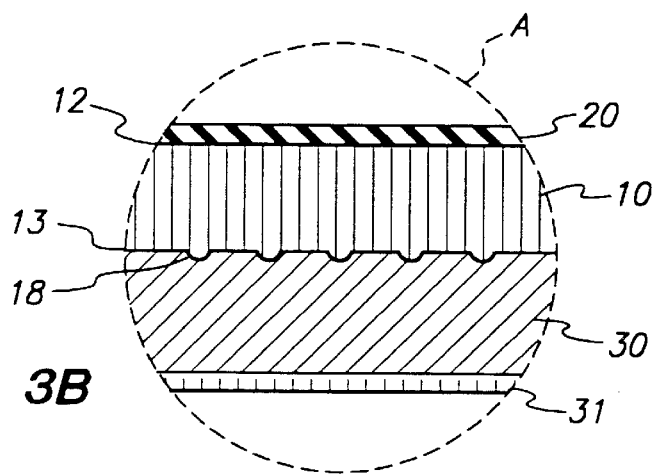
Figure 3C:
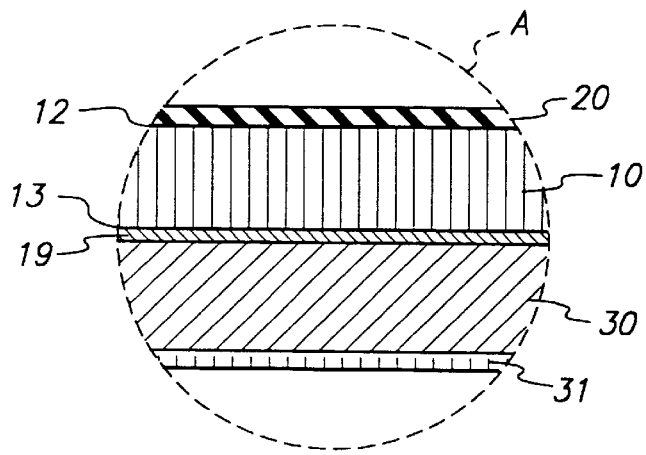

Referring now to FIGS. 3A–C, the portion of stent 10 encircled in region A of FIG. 2C is described for three illustrative embodiments of the present invention. Each of FIGS. 3A–3C shows a different possible outside surface treatment for stent 10.

In FIG. 3A, stent 10 includes cross axial grooves 17 on its outside surface. Expansion of balloon 20 pushes stent 10 into intimate contact with stenosis 30. The inside surface 12 of the stent is in contact with the balloon and is preferably smooth to yield a low coefficient of friction, as discussed generally hereinabove. Outside surface 13 of stent 10 includes irregular macroscopic cross-axial grooves 17 on its outer circumference.

In FIG. 3B, a different embodiment of the stent is described, with common elements indicated by like numbers. Outside surface 13 of stent 10 includes irregular macroscopic cross-axial protrusions 18. Like the macroscopic grooves 17 of the embodiment of FIG. 3A, macroscopic protrusions 18 in FIG. 3B provide a peak and valley structural interaction with stenosis 30. This interaction increases the surface area of contact between lesion 30 and stent 10, thus raising the coefficient of friction therebetween.

In FIG. 3C, a third illustrative alternative embodiment is described wherein stent 10 incorporates adhesive coating 19 on its outside surface 13. Outside surface 13 of stent 10 is coated with a suitable biocompatible adhesive material 19 that provides some or all of the following benefits: an increase in the frictional coefficient, a physical interleaving with the vessel tissue to form a series of peaks and valleys, or creation of an adhesive bond between the stent and the vessel wall.

While one application for the above-described stent includes treatment of cardiovascular disease such as atherosclerosis or other forms of coronary narrowing, the present invention may also be used for treatment of narrowed vessels in other components of the vascular system, for example, the kidney, leg, carotid artery, or elsewhere in the body. As will of course be appreciated, the size of the stent, as well as its external characteristics, may need to be adjusted to compensate for the differing sizes of the vessel to be treated.

While this invention has been described in connection with an illustrative preferred embodiment thereof, modifications and changes may be made thereto by those skilled in the art without departing from the spirit and scope of the invention. Accordingly, the scope of this invention is to be limited only by the appended claims.

What is claimed is:

1. A stent for implanting in a vessel within the human body, the vessel having a vessel surface, the stent comprising:

an expandable, generally cylindrical segment defining an inside surface and an outside surface and comprising a plurality of substatially straight, non-overlapping wire-like segments connected at a plurality of apices, the inside surface being regular and smooth to yield a low coefficient of friction, the outside surface being treated to yield a higher coefficient of friction with the surface;

wherin the outside surface includes a macroscopic surface modification comprising a multiplicity of substantially uniformly axially oriented features.

2. The stent as defined in claim 1 wherein the macroscopic surface modification comprises cross-axial grooves.

3. A stent for implantation into a vessel having a vessel surface, the stent having an expandable, generally seamless cylindrical body portion defining an inside surface and an outside surface, the inside surface being regular and smooth to provide a low coefficient of friction, the outside surface being treated to yield a higher coefficient of friction with the vessel surface;

the outside surface comprising a macroscopic surface modification that engages the vessel surface, the macroscopic surface modification comprising a multiplicity of substantially uniformly cross-axial features.

4. The stent as defined in claim 3 wherein the microscoptic surface modification comprises cross-axial grooves.

5. An endovascular support device for implantation in a vessel within the human body, the vessel having an inner vessel surface, the endovascular support device comprising:

a generally cylindrical body portion defining an inside surface and an outside surface, the body portion expandable from a first diameter to a second diameter; and wherein the outside surface includes a macroscopic surface modification that engages the inner vessel surface to yield an increased frictional force between the outside surface of the endovascular support device and the inner surface of the vessel, the macroscopic surface modification comprising at least one axially-oriented feature.

6. The endovascular support device as defined in claim 5 wherein the at least one axially-oriented feature comprises at least on cross-axial groove.

7. An expandable generally cylindrical coronary stent for implantation in a vessel within the coronary vasculature, the stent comprising:

an inside surface and an outside surface, the outside surface comprising a macroscopic modification that engages the vessel surface, the macroscopic surface modification comprising a multiplicity of axially-oriented grooves that increase the surface area in contact with the vessel.

* * * * *